(12) United States Patent
Miyamoto et al.

(10) Patent No.: US 6,462,093 B1
(45) Date of Patent: *Oct. 8, 2002

(54) METHOD FOR CONVERTING SPARINGLY WATER-SOLUBLE MEDICAL SUBSTANCE TO AMORPHOUS STATE

(75) Inventors: Misao Miyamoto, Funabashi (JP); Toshihisa Oda, Funabashi (JP)

(73) Assignee: Nissan Chemical Industries, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/011,060

(22) PCT Filed: Aug. 8, 1996

(86) PCT No.: PCT/JP96/02246
§ 371 (c)(1),
(2), (4) Date: Feb. 6, 1998

(87) PCT Pub. No.: WO97/06781
PCT Pub. Date: Feb. 27, 1997

(30) Foreign Application Priority Data

Aug. 11, 1995 (JP) ............................................. 7-205936
Nov. 29, 1995 (JP) ............................................. 7-310400
Nov. 29, 1995 (JP) ............................................. 7-310401

(51) Int. Cl.[7] .............................................. A61K 47/30
(52) U.S. Cl. ................. 514/772.3; 514/772; 514/772.1; 514/772.2; 514/777; 514/781; 524/2; 524/211; 424/484; 424/486; 424/487; 424/488; 424/489; 424/500; 424/501
(58) Field of Search ................................. 424/465, 400, 424/484, 486, 489, 488, 494; 524/2, 211; 514/781, 772.3, 777

(56) References Cited

U.S. PATENT DOCUMENTS 2,373,049 A * 4/1945 Pedersen ..................... 524/211
4,083,814 A * 4/1978 Mark et al. ................. 524/211
4,412,986 A * 11/1983 Kawata et al. .............. 514/781
4,654,206 A * 3/1987 Okuda et al. ............... 514/781
4,695,591 A * 9/1987 Hanna et al. ............... 514/781
4,704,285 A * 11/1987 Alderman et al. .......... 514/781
4,857,336 A * 8/1989 Khanna et al. ............. 424/473
5,211,957 A * 5/1993 Hagelmann et al. ........ 424/466
5,326,570 A * 7/1994 Rudnic et al. .............. 424/465
5,340,591 A    8/1994 Nakano et al.
5,510,115 A * 4/1996 Breillatt, Jr. et al. ....... 424/473
5,705,190 A * 1/1998 Broad et al. ................ 424/465
5,714,157 A * 2/1998 Sandell et al. ............. 424/409
5,858,412 A * 1/1999 Staniforth et al. .......... 424/489

FOREIGN PATENT DOCUMENTS

| EP | 0 344 603 A1 | 12/1989 |
| JP | A-63-115815 | 5/1988 |
| JP | A-2-67229 | 3/1990 |
| JP | A-5-262642 | 10/1993 |
| JP | A-5-306225 | 11/1993 |
| WO | WO 92/18106 | 10/1992 |
| WO | WO 94/14421 | 7/1994 |
| WO | WO 94/19411 | 9/1994 |

OTHER PUBLICATIONS

US Pharmacopeia p. 1730, Jan. 2000.*

* cited by examiner

Primary Examiner—Thurman K. Page
Assistant Examiner—Liliana Di Nola-Baron
(74) Attorney, Agent, or Firm—Oliff & Berridge, PLC

(57) ABSTRACT

A process for producing a solid dispersion of a sparingly water-soluble medical substance which comprises subjecting the sparingly water-soluble medical substance, an amorphous state-inducing agent and an amorphous state-stabilizing agent to heat treatment or mechanochemical treatment; and a process for producing a solid dispersion of a sparingly water-soluble medical substance which comprises high-frequency heating the sparingly water-soluble medical substance and an amorphous state-stabilizing agent. These processes make it possible to make sparingly water-soluble medical substance amorphous at a temperature lower than those employed in the conventional methods. The solid dispersions of the armorphous sparingly water-soluble medical substances thus obtained have an improved mucosal or rectal absorption rate, which makes it possible to elevate their bioavailability.

12 Claims, No Drawings

METHOD FOR CONVERTING SPARINGLY WATER-SOLUBLE MEDICAL SUBSTANCE TO AMORPHOUS STATE

This application is a 371 of PCT/JP96/02246 filed Aug. 8, 1996.

TECHNICAL FIELD

The present invention relates to a technique for effectively utilizing a sparingly-water soluble medical substance, particularly to a method for producing a solid dispersion using a novel method for converting it to the amorphous state. This technique can be used in the field in which a medical substance should be eluted, for example, the fields of agricultural chemicals, perfumery and cosmetics, and medical treatment, particularly medical treatment.

BACKGROUND ART

For designing pharmaceutical preparations for oral administration, it is important to increase biological availability of sparingly water-soluble medical substance by improving their solubility and absorptivity from the viewpoint of efficacy and safety of pharmaceutical preparations.

As a measure to increase the biological availability of a sparingly water-soluble medical substance, there are a method in which particles of a medical substance are subjected to supermicro-particle powdering and a wettability or a dispersibility is improved, and a method in which a solubility of an original medical substance is improved by formation of a solid dispersion. A method in which a solid dispersion is formed by rendering a medical substance amorphous attracts special attention. The solid dispersion is a substance obtained by dispersing a medical substance into a carrier in a monomolecular state. In this dispersion, the medical substance is retained in a completely amorphous state. In general, an amorphous form is, compared to a crystal form, in a high energy state, and is therefore expected to have a high absorptivity.

The methods of producing a solid dispersion are roughly classified into a solvent method, a melting method (a heating method), a melting-solvent method, a mechanochemical method, and the like.

The solvent method comprises dissolving in an organic solvent both of a medical substance and a water-soluble polymer base which serves as an amorphous state-stabilizing agent and then, in the presence of core granules or as it is, distilling off the solvent to obtain a solid dispersion. This method is excellent in improvement of solubility of a sparingly water-soluble medical substance. It is, however, disadvantageous in that a high production cost is required because a large amount of an organic solvent is used and that there is a case in which the solvent remaining in the pharmaceutical preparation is concerned.

The melting method (the heating method) utilizes depression of the melting point of a mixture of a medical substance and a water-soluble polymer base which serves as an amorphous state-stabilizing agent. It comprises kneading both materials under heating at the temperature lower than their melting points, allowing the medical substance to disperse in a molecular state, followed by cooling, solidifying, and pulverizing the mixture.

The melting method is excellent in that no organic solvent is used. However, some sparingly water-soluble medical substances are not converted to the amorphous state sufficiently by adding only an amorphous-state stabilizing agent as a solid dispersion carrier.

Further, in order to completely convert a medical substance to the amorphous state, it is necessary to knead the mixture at a high temperature but lower than the melting points of the medical substance and the solid dispersion carrier. Thus, there are some cases that not only the medical substance is decomposed and the carrier is deteriorated but also the medical substance is not converted to the amorphous state sufficiently.

For example, in the method where a medical substance and a water-soluble polymer base which serves as an amorphous state-stabilizing agent are melted under heating to utilize depression of the melting point of the mixture, the melting point is depressed at most about 10° C. and a high temperature is still necessary for the heat treatment. In addition, since many polymer bases are originally amorphous, its apparent melting viscosity is high and microdispersity of the medical substance and the water-soluble polymer is poor. Thus, some medical substances cannot be converted to the amorphous state sufficiently.

An attempt has been made to melt a medical substance under heating together with a low molecular weight compound such as phosphatidylcholine as an amorphous state-inducing agent in place of a water-soluble polymer base as a solid dispersion carrier. However, in this method, the heat treatment may possibly cause decomposition and denaturation of a medical substance. Further, when the temperature of the heat-treated product is cooled to the room temperature, it is concerned that the resulting product shows such poor stability that it hardly keeps its amorphous state.

The mechanochemical method (treatment) comprises using mechanical energy such as compression, shearing, and friction to enhance a medical substance in a solid state to become amorphous and to improve dispersion of the resulting amorphous medical substance to the carrier, thereby obtaining a solid dispersion. Specifically, the treatments includes mixing and pulverization with a ball mill, treatment with a planetary mill, treatment with a compression press, mixing treatment with a shear roll, and the like.

The mechanochemical treatment alone is difficult to completely convert a sparingly water-soluble medical substance to the amorphous state even when an amorphous state-stabilizing agent is added to a medical substance. This may be because the level of mechanical energy is low. In such a case, a specific machine is sometimes required (WO 92/18106).

As described above, it has been desired to develop a method for obtaining a solid dispersion of a sparingly water-soluble medical substance in a complete amorphous state inexpensively compared with the conventional methods in an industrial scale.

DISCLOSURE OF THE INVENTION

As a result of intensive investigation to overcome the problems of the conventional methods, the present inventors have found a method for converting a sparingly water-soluble medical substance to the amorphous state which comprises mixing these components of (1) a sparingly water-soluble medical substance, (2) an amorphous state-inducing agent and (3) an amorphous state-stabilizing agent, and subjecting the resulting mixture to heat treatment or mechanochemical treatment. Further, it has been found that high-frequency heating is preferred as the heat treatment to the conventional heating by a heater or steam.

In addition, the inventors have found a method of converting a sparingly water-soluble medical substance to the amorphous state which comprises mixing two components of (1) a sparingly water-soluble medical substance and (3) an amorphous state-stabilizing agent and subjecting the mixture to high-frequency heating.

Furthermore, it is possible to produce a pharmaceutical preparation of a sparingly water-soluble medical substance containing a solid dispersion obtained by the method of converting the medical substance to the amorphous sate according to the present invention.

The (1) sparingly water-soluble medical substance used in the present invention is a medical substance that has extremely low water-solubility and is hardly absorbed from the intestine, tunica mucosa nasi, rectum, and the like. It is difficult to improve absorptivity of such medical substances by the conventional techniques for formulating them into the pharmaceutical preparations. Absorptivity of these medical substances can be improved by converting them to the amorphous state. Examples of the sparingly water-soluble medical substances include dihydropyridine compounds such as nifedipine, nicardipine, hydrochloride, or the like, phenacetin, digitoxin, diazepam, phenytoin, tolbutamide, theophylline, griseofulvin, chloramphenicol, and the like.

The (2) amorphous state-inducing agent used in the present invention can be any compound capable of depressing the melting point of the mixture of it with a medical substance. A crystalline compound is particularly preferred. This is a compound having functions and properties to change crystal-lattice energy of a sparingly water-soluble medical substance to a direction of low energy and to increase fluctuation of crystal lattice at the same temperature in the presence of heat or mechanical energy. The amorphous state-inducing agent varies depending on the sparingly water-soluble medical substance to be used. For example, it is preferable to use a neutral substance or an acidic substance, particularly an acidic substance in the case of a) a basic sparingly water-soluble medical substance, and a neutral substance or a basic substance, particularly a basic substance in the case of b) an acidic sparingly water-soluble medical substance.

Specific examples of the amorphous state-inducing agents include amino acid or its salt (such as aspartic acid or its Na salt, Mg salt, or the like, glycine, alanine, glutamic acids, glutamic acid hydrochloride, or the like), Aspartame, erythorbic acid or its salt (such as an Na salt or the like), ascorbic acid or its salt (such as an Na salt or the like), stearic acid ester, aminoethylsulfonic acid, inositol, ethylurea, citric acid or its salt (such as an Na salt, e.g., tri Na salt, di Na salt, dihydrogen Na salt, etc., a Ca salt or the like), glycyrrhizinic acid or its salt (such as an Na salt, e.g., tri Na salt, di Na salt, etc., an ammonium salt, e.g., diammonium, monoammonium, etc., a K salt, or the like), gluconic acid or its salt (such as an Na salt, a Ca salt, an Mg salt, or the like), creatinine, salicylic acid or its salt (such as an Na salt or the like), tartaric acid or its salt (such as an Na salt, a K.Na salt, a hydrogen.K salt, or the like), succinic acid or its salt (such as Na salt, e.g., di Na salt, mono Na salt, etc.), calcium acetate, sodium saccharin, aluminum hydroxide, sorbic acid or its salt (such as a K salt or the like), dehydroacetic acid or its salt (such as an Na salt or the like), sodium thiomalate, nicotinic acid amide, urea, fumaric acid or its salt (such as an Na salt or the like), macrogols, maltose, maltol, maleic acid, mannitol, meglumine, sodium desoxycholate, phosphatidylcholine and the like.

Preferable examples thereof include amino acid or its salt (such as aspartic acid or its Na salt, Mg salt, or the like, glycine, alanine, glutamic acids, glutamic acid hydrochloride, or the like), ascorbic acid or its salt (such as an Na salt or the like), stearic acid ester, aminoethylsulfonic acid, ethylurea, citric acid or its salt (such as an Na salt, e.g., tri Na salt, di Na salt, dihydrogen Na salt, etc., a Ca salt, or the like), glycyrrhizinic acid or its salt (such as an Na salt, e.g., tri Na salt, di Na salt, etc., an ammonium salt, e.g., diammonium, monoammonium, etc., a K salt, or the like), creatinine, tartaric acid or its salt (such as an Na salt, a K.Na salt, a hydrogen.K salt, or the like), succinic acid or its salt (such as an Na salt, e.g., di Na salt, mono Na salt, etc.), urea, fumaric acid or its salt (such as an Na salt or the like), macrogols, maltose, maltol, mannitol, meglumine, and the like.

More preferably, the amorphous state-inducing agents include amino acid or its salt (such as aspartic acid or its Na salt, Mg salt, or the like salt, glycine, alanine, glutamic acids, glutamic acid hydrochloride, and the like), ethylurea, glycyrrhizinic acid or its salt (such as an Na salt, e.g., tri Na salt, di Na salt, etc., an ammonium salt, e.g., diammonium, monoammonium, etc., a K salt, or the like), tartaric acid or its salt (such as an Na salt, a K.Na salt, a hydrogen.K salt, or the like), succinic acid or its salt such as an Na salt (e.g., di Na salt, mono Na salt, etc.), urea, maltose, maltol, mannitol, meglumine, and the like.

Most preferably, the agents are glycyrrhizinic acid or its salt (such as an Na salt, e.g., tri Na salt, di Na salt, etc., an ammonium salt, e.g., diammonium, monoammonium, etc., a K salt, or the like), succinic acid or its salt (such as an Na salt, e.g., di Na salt, mono Na salt, etc.), urea, maltol, mannitol, and the like.

Depression of melting point of the mixture of the amorphous state-inducing agent and the sparingly water-soluble medical substance varies depending on the sparingly water-soluble medical substance to be mixed. It is preferable to use a compound which can depress the melting point of the mixture to 5° C. or more from that of the sparingly water-soluble medical substance.

It is more preferable to use a compound which can depress the melting point of the mixture of the amorphous state-inducing agent and the sparingly water-soluble medical substance to 15° C. or more, particularly 25° C. or more, from the melting point of the sparingly water-soluble medical substance.

In the case of the high-frequency heating, the sparingly water-soluble medical substance can be converted to the amorphous state by heating the mixture of the sparingly water-soluble medical substance and the amorphous state-stabilizing agent under high frequency without using the amorphous state-inducing agent. As a matter of course, the mixture of the three components containing the amorphous state-inducing agent can also provide satisfactory results when subjected to high-frequency heating.

Following that the crystalline structure of the sparingly water-soluble medical substance is fluctuated by the amorphous state-inducing agent, the amorphous state-stabilizing agent interacts with the fluctuated state of the crystal lattice to stabilize the amorphous state.

Accordingly, any amorphous state-stabilizing agent can be used in the present invention as long as it has the above-described function. In other words, any compound having a functional group capable of interacting with the sparingly water-soluble medical substance can be used as the amorphous state-stabilizing agent. It is preferable to use a highly thermostable compound having a functional group that is flexible and highly miscible with the sparingly water-soluble medical substance, for example, the following amorphous polymer base. The compound miscible with the sparingly water-soluble medical substance means the compound having solubility parameter (Solubility Parameter: Encyclopedia of Polymer Science and Engineering, vol. 15, p. 393, John Wiley & Sons,Inc. 1989) close to that of the sparingly water-soluble medical substance. More preferably, the amorphous state-stabilizing agent is highly miscible with not only the sparingly water-soluble medical substance but also the amorphous state-inducing agent.

In addition, the functional group of the amorphous state-stabilizing agent which conducts interacting action with and is selected depending on the sparingly water-soluble medical substance to be used. For example, it is preferably to select a neutral substance or an acidic substance, particularly an acidic substance, in the case of a) a basic sparingly water-soluble medical substance and a neutral substance or a basic substance, particularly a basic substance, in the case of b) an acidic sparingly water-soluble medical substance.

Examples of (3) the amorphous state-stabilizing agents used in the present invention include cellulose derivatives (such as hydroxyethylcellulose, hydroxypropylmethylcellulose (HPMC), hydroxypropylcellulose (HPC), hydroxypropylmethylcellulose-acetate succinate (HPMC-AS), methylcellolose, ethylcellulose, carboxymethylcellulose, phthalic acetate cellulose, or the like), polyvinyl pyrrolidone, cross-linked polyvinyl pyrrolidone, polyvinyl alcohol, polyvinyl acetate, vinyl alcohol/vinyl acetate copolymer, ethylene/vinyl acetate copolymer, polyethylene oxide derivatives (such as polyethylene glycol, polyoxy ethylene polyoxy propylenecetyl ether, polyoxy ethylene alkyl ether, polyoxy ethyleneoctyl phenyl ether, polyoxy ethyleneoleyl amine, polyoxy ethyleneoleyl ether, polyoxy ethyleneoleyl ether sodium phosphate, polyoxy ethylene hydrogenated castor oil, polyoxy ethylene stearyl ether, polyoxy ethylene stearyl ether phosphoric acid, polyoxy ethylene cetyl ether, polyoxy ethylene cetyl ether sodium phosphate, polyoxy ethylene sorbitol bees wax, polyoxy ethylenenonyl phenyl ether, polyoxy ethylene castor oil, polyoxy ethylenebehenyl ether, polyoxy ethylene polyoxy propyleneglycol, polyoxy ethylene polyoxy propylenecetyl ether, polyoxy ethylene lauryl ether, polyoxyethylene. lanoline, polysorbate 40, polysorbate 60, polysorbate 65, polysorbate 80, or the like), sodium polystyrene sulfonate, gelatin, soluble starch, pullulan, dextran, gum arabic, chondroitin sulfuric acid or its Na salt, hyaluronic acid, pectin, chitin, chitosan, $\alpha$, $\beta$ or $\gamma$-cyclodextrin, alginic acid derivatives (such as alginic acid, its Na salt, propylene glycol ester, or the like), acryl resins (such as homopolymer of methacrylic acid derivative and/or acrylic acid derivative, e.g., methacrylic acid, methyl methacrylate, butyl methacrylate, dimethylaminoethyl methacrylate, ethyl trimethyl chloride ammonium methacrylate, acrylic acid, ethyl acrylate, etc. and copolymer of methacrylic acid derivative and/or acrylic acid derivative, e.g., aminoalkyl/methacrylate copolymer, methylmethacrylate/methacrylic acid copolymer, methacrylic acid/ethyl acrylate copolymer, methacrylic acid/n-butyl acrylate copolymer, acrylic acid ester/vinyl acetate copolymer, 2-ethylhexyl acrylate/vinyl pyrrolidone copolymer, starch acrylate, etc.) and polyvinyl acetal diethylaminoacetate and the like.

In addition, compounds capable of forming gel, such as silicon dioxide, aluminum hydroxide, or the like, can be also used as the amorphous state-stabilizing agent according to the present invention.

Preferable examples of the amorphous state-stabilizing agents include hydroxyethylcellulose, hydroxypropylmethylcellulose (HPMC), hydroxypropylcellulose (HPC), hydroxypropylmethylcellulose-acetate succinate (HPMC-AS), polyvinyl pyrrolidone, sodium polystyrenesulfonate, dextran, $\alpha$, $\beta$ or $\gamma$-cyclodextrin, acrylic resins (such as homopolymer and/or copolymer of methacrylic acid derivative and/or acrylic acid derivative, e.g., methacrylic acid, methyl methacrylate, butyl methacrylate, dimethylaminoethyl methacrylate, ethyl trimethyl chloride ammonium methacrylate, acrylic acid, ethyl acrylate, etc.), and polyvinyl acetal diethylamino acetate and the like.

More preferably, the amorphous state-stabilizing agents include hydroxypropylmethylcellulose (HPMC), hydroxypropylmethyl cellulose-acetate succinate (HPMC-AS), polyvinyl pyrrolidone, acrylic resins (such as homopolymer and/or copolymer of methacrylic acid derivative and/or acrylic acid derivative, e.g., methacrylic acid, methyl methacrylate, butyl methacrylate, dimethylaminoethyl methacrylate, ethyl trimethyl chloride ammonium methacrylate, acrylic acid, ethyl acrylate, etc.), and polyvinyl acetal diethylamino acetate and the like.

Sort and ratio of compounding (1) the sparingly water-soluble medical substance, (2) the amorphous state-inducing agent, and (3) the amorphous state-stabilizing agent used in the present invention can be appropriately selected depending on the sparingly water-soluble medical substance to be used. The weight ratio of (1):(2):(3) is generally 1:(0.1–10): (0.1–10), preferably the (1):(2):(3) being 1:(0.3–3):(0.3–8), and more preferably the (1):(2):(3) being 1:(0.3–2):(0.5–5).

The solid dispersion of the sparingly water-soluble medical substance according to the present invention can be obtained by granulating (mixing) the essential components, (1) the sparingly water-soluble medical substance, (2) the amorphous state-inducing agent, and (3) the amorphous state-stabilizing agent, by means of the wet or dry method, at the same time or after the mixing, heat-treating the mixture at the temperature that is not less than the temperature at which the amorphous state-induction initiates and that the sparingly water-soluble medical substance is not deteriorated by decomposition, or subjecting the mixture to the mechanochemical treatment under the same energic conditions as the heat treatment. In this occasion, the mixture is preferably heated at the temperature not more than the melting point of the sparingly water-soluble medical substance. The temperature is closest to the amorphous state-induction initiating temperature as much as possible. If the heating temperature is lower, for example, 5 to 10° C. lower than the amorphous state-induction initiating temperature, conversion to the amorphous state does not proceed sufficiently.

The amorphous state-induction initiating temperature means the endothermic reaction initiating temperature (peak rise temperature) which is observed when 10 mg of the sample of the mixture (1:1) of the sparingly water-soluble medical substance and the amorphous state-inducing agent is measured at the temperature rising rate 10° C./minute using a differential scanning calorimeter (DSC).

The granulation (mixing) does not require any special means and is conducted using a universal mixer, a fluidized bed granulation machine, a dash mill, a wet granulation machine, a roller compacted granulation machine or the like. The heat treatment may be carried out together with the granulation. Alternatively, the heat treatment may be carried out after the granulation by the usual heating method, such as heating by a heater, steam, infrared rays, extreme infrared rays, or the like, using, for example, a hot air dryer, a fluidized bed dryer, a gyro-dryer, a powder dryer, or the like.

The conversion to the amorphous state can be conducted also by the mechanochemical treatment with not only the heat in the heat treatment, but also mechanical energy of compression, shearing, friction or the like as an energy to be added. For example, the conversion to the amorphous state can also be conducted, without heating the above-mentioned essential components, only through the mechanochemical treatment such as pulverization with a ball mill, treatment with a planetary mill, treatment with a compression press, treatment with a shear roll, treatment with a kneader or the like. This method makes it easy to control formation of thermal decomposed substance.

In addition, it is possible to apply oscillation energy such as ultrasonic wave, or electromagnetic energy such as electrical field, magnetism, or the like, as energy to fluctuate the crystal lattice of the sparingly water-soluble medical substance in the three-component mixture.

Either the heat treatment or the treatment with the mechanical energy under the same energy conditions as the heat treatment can be carried out at the amorphous state-induction temperature. The treatment time required for conversion to the amorphous state ranges generally from 20 to 120 minutes, preferably 30 to 90 minutes, in the case of the heat treatment, and generally from 1 to 20 minutes, preferably 3 to 10 minutes, in the case of the mechanical energy treatment, in view of quality control, homogeneity, and energy saving.

The heat treatment can be effected by using high frequency heating as well as the above-described heating methods.

The high-frequency heating according to the present invention can be carried out by any of high-frequency dielectric heating, radiofrequency inductive heating, plasma heating, and the like, with being high-frequency dielectric heating particularly preferred.

The frequency zone can be selected depending on a substance to be heated. Microwave heating using a microwave zone is especially preferable. Four frequencies which are distributed as ISM (Industrial, Scientific and Medical) frequencies under the Wireless Telegraphy Act, namely, 915, 2450, 5800 and 22125 MHz can be used as the frequency in the microwave heating. Generally, the frequency, 915 or 2450 MHz can be used.

The microwave heating can be conducted using an oven system (electronic oven system or conveyor system) or a wave guide system depending on a shape of a substance to be heated.

In the case of high-frequency heating, the amorphous state-inducing agent is not an essential component. Sort and rate of compounding the other two components, (1) the sparingly water-soluble medicl substance and (3) the amorphous state-stabilizing agent, are generally (1):(3)=1:(0.1–10), preferably the (1):(3) being 1:(0.3–8), more preferably the (1):(3) being 1:(0.5–5) though they are appropriately selected depending on the sparingly water-soluble medical substance to be used.

In this case, the solid dispersion of the sparingly water-soluble medical substance can be obtained by granulating (mixing) (1) the sparingly water-soluble medical substance and (3) the amorphous state-stabilizing agent by the wet or dry method, and simultaneously or thereafter, conducting high-frequency heating.

The treatment time required for conversion to the amorphous state ranges from 3 to 40 minutes, preferably 5 to 30 minutes, in the case of the batch treatment, in view of quality control, homogeneity, and the like though it varies depending on high frequency power. The treatment required in the continuous treatment using the conveyer system can be calculated from the energy necessary for converting to the amorphous state in the batch treatment. In the case of the high-frequency heating, a highly homogeneous solid dispersion can be obtained for a short period of time compared with the usual heat treatment.

The granulation (mixing) is conducted by using a universal mixer, a fluidized bed granulation machine, a dash mill, a wet granulation machine, a roller compacted granulation machine or the like, without the necessity of special measures. The granulation may be effected simultaneously with the usual heat treatment or the above-described mechanochemical treatment, such as pulverization with a ball mill, treatment with a planetary mill, treatment with a compression press, treatment with a shear roll, treatment with a flow coater, treatment with a kneader, or the like. Alternatively, after granulation, the usual heat treatment using a hot air dryer, a fluidized bed dryer, a gyro-dryer, a powder dryer, and the like, or the above-described mechanochemical treatment may be carried out.

Further, it is possible to perform. the heat treatment, the high-frequency heating, and the mechanochemical treatment in combination.

For the conversion of the sparingly water-soluble medical substance to the amorphous state according to the present invention, it is possible to contain water, a surfactant, an antioxidant, a preservative, a stabilizer, and the like components other than the three components, (1) the sparinly water-soluble medical substance, (2) the amorphous state-inducing agent, and (3) the amorphous state-stabilizing agent to effect the conversion to the amorphous state. Further, with respect to (2) the amorphous state-inducing agent and (3) the amorphous state-stabilizing agent, it is possible to incorporate one component or two or more components to allow the conversion to the amorphous state.

In the process for producing the solid dispersion obtained by the method of conversion to the armorphous state and the oral administration containing the solid dispersion in the. present invention, it is possible to add a pharmaceutical excipient (for example, crystalline cellulose and lactose), a disintegrant, a lubricant and/or a colorant which are generally known in the field of preparations, as required.

BEST MODE FOR CARRYING OUT THE INVENTION

The following Examples will be given to demonstrate the necessity of the three essential components (1) the sparingly water-soluble medical substance, (2) the amorphous state-inducing agent and (3) the amorphous state-stabilizing agent, the heat or mechanochemical treatment, and the necessity of the high-frequency heating of (1) the sparingly water-soluble substance and (3) the amorphous state-stabilizing agent in the present invention.

Test Method 1

Ten mg of a sample is measured with a differential scanning calorimeter (DSC) at a temperature rising rate of 10° C./minute. The temperature at the tip of the endothermic peak is regarded as the melting point. The mixture of a sparingly water-soluble medical substance and an amorphous state-inducing agent (1:1) is used as a sample and the endothermic reaction initiating temperature (peak rise temperature) which is observed when measured using a differential scanning calorimeter (DSC) is regarded as the amorphous state-induction initiating temperature.

Test Method 2

Crystallinity is determined by measuring powder X-ray diffractometry. A sample of the three component mixture containing a sparingly water-soluble medical substance, an amorphous state-inducing agent and an amorphous state-stabilizing agent is subjected to powder X-ray diffractometry to read a diffraction intensity (S0) at a diffraction angle of 2θ derived from crystals of the sparingly water-soluble medical substance. Similarly, the diffraction intensity (S1) is measured for the sparingly water-soluble medical substance in the sample which has been subjected to the heat treatment or the like to plot S0 as abscissa axis and S1 as ordinate axis, per corresponding crystal peak. One hundred times the slope approximated by the regression line passing through the origin is taken as crystallinity (%). For example, when crystallinity does not change, namely keeps 100%, the angle of elevation of the regression line is 45° and the slope is 1. When crystallinity is 10%, the slope is 0.1.

EXAMPLE 1

Five g of water was added to a mixture of 10 g of nifedipine, 10 g of succinic acid, and 20 g of HPMC-AS. The resulting mixture was subjected to wet granulation and heated at 160° C. for 1 hour to obtain a solid dispersion. The thus-obtained solid dispersion did not show the peak derived from crystals of nifedipine. This was pulverized by the conventional method. The melting point of nifedipine was 175° C., that of succinic acid was 192° C., and that of the mixture of nifedipine and succinic acid was 167° C. The amorphous state induction initiating temperature was 158° C.

EXAMPLE 2

A mixture of 150 g of nicardipine hyrochloride, 100 g of urea, and 150 g of hydroxypropylmethylcellulose (HMPC) was heat-treated with a hot air dryer at atmospheric pressure and at 115° C. for 1 hour to obtain a solid dispersion. The resulting solid dispersion did not show the peak derived from crystals of nicardipine hydrochloride.

The melting points of nicardipine hydrochloride, urea, and the mixture of nicardipine hydrochloride and urea were 170° C., 137° C. and 129° C., respectively. The amorphous state induction initiating temperature was 115° C.

After adding 100 g of crystalline cellulose and 100 g of lactose to 300 g of the solid dispersion, the mixture was subjected to dry granulation by the conventional method and tabletted to obtain solid tablets.

EXAMPLE 3

A mixture of 3 g of nicardipine chloride, 1.5 g of urea, and 5.5 g of HPMC was treated with a high-speed planetary mill at 100 G for 3 minutes. As a result of powder X-ray diffractometry, no peak derived from crystals could be observed.

EXAMPLE 4

Instead of the heat treatment at 160° C. for 1 hour in Example 1, the mixture was heat-treated by microwave for 20 minutes (700 W) using a microwave dryer (frequency of 2450 MHz) to obtain a solid dispersion. The resulting solid dispersion was amorphous without showing the peak derived from crystals of nifedipine.

EXAMPLE 5

To 20 g of water were added 20 g of nicardipine hydrochloride, 40 g of hydroxypropylmethylcellulose-acetate succinate (HPMC-AS) followed by wet granulation. The resulting product was heated by microwave (700 W) for 15 minutes using a microwave dryer (frequency of 2450 MHz) to obtain a solid dispersion. The resulting solid dispersion did not show a peak derived from crystals of nicardipine hydrochloride.

After adding 50 g of crystalline cellulose and 50 g of lactose to 50 g of the solid dispersion, the mixture was subjected to dry granulation by the conventional method and tabletted to obtain solid tablets.

EXAMPLE 6

Five g of water was added to 3 g of tolbutamide and 6 g of hydroxypropylmethylcellulose-acetate succinate (HPMC-AS) and mixed in a mortar. The resulting mixture was heat-treated by microwave for 20 minutes (500 W) using a microwave dryer (frequency of 2450 kHz) to obtain a solid dispersion. The thus-obtained solid dispersion did not show a peak attributed to crystals of tolbutamide.

EXAMPLE 7

Five g of theophylline, 2 g of succinic acid, and 15 g of polyvinyl pyrrolidone were subjected to dry granulation and heat treatment by microwave for 20 minutes (500 W) using a microwave dryer (frequency of 2450 kHz) to obtain a solid dispersion. The resulting solid dispersion did not show a peak attributed to crystals of theophylline.

Comparative Example 1

The procedure of Example 1 was repeated except that anyone of the following in Example 1 was altered.
- 1-A: only exclusive of succinic acid (the amorphous state-inducing agent)
- 1-B: only exclusive of HPMC-AS (the amorphous state-stabilizing agent)
- 1-C: heat-treated at 140° C. (which is lower than the amorphous state induction initiating temperature of 158° C.

In each case, the sample was not completely converted to the amorphous state and was not a complete solid dispersion.
Crystallinity of Nifedipine
- Example 1: No peak derived from crystals could be observed.
- Comparative Example 1-A: 50%
- Comparative Example 1-B: A powder X-ray diffractometory peak different from that of nifedipine was observed.
- Comparative Example 1-C: 100%

Comparative Example 2

The procedure of Example 2 was repeated except that any one of the following in Example 2 was altered.
- 2-A: only exclusive of urea (the amorphous state-inducing agent)
- 2-B: only exclusive of HPMC (the amorphous state-stabilizing agent)
- 2-C: heat-treated at 100° C. (which is lower than the amorphous state induction initiating temperature of 115° C.)

In each case, the sample was not completely converted to the amorphous state and was not a complete solid dispersion.
Crystallinity of Nicardipine Hydrochloride
- Example 2: No peak derived from crystals could be observed.

Comparative Example 2-A: 85%

Comparative Example 2-B: A powder X-ray diffractometry different from that of nicardipine hydrochloride was observed.

Comparative Example 2-C: 95%

Comparative Example 3

The same procedure as in Example 3 was conducted except for excluding urea (the amorphous state-inducing agent). As a result of powder X-ray diffractometry, crystallinity was 80%.

Comparative Example 4

The same procedure as in Example 2 was conducted except for heat treating at 115° C. for 1 hour using a hot air dryer in place of the heat treatment by microwave of the Example 5.

Crystallinity of nicardipine hydrochloride was 70% and the product was not a complete solid dispersion.

INDUSTRIAL APPLICABILITY

Since the present invention is constituted as described above, a sparingly water-soluble medical substance can be produced as an amorphous solid dispersion. Thus, it is expected to increase biological availability of a sparingly water-soluble medical substance by improving its solubility and absorptivity.

What is claimed is:

1. A method for producing a solid dispersion of a sparingly water-soluble medical substance comprising heat treating a sparingly water-soluble medical substance, an amorphous state-inducing agent selected from the group consisting of amino acid or its salt, Aspartame, erythorbic acid or its salt, ascorbic acid or its salt, stearic acid ester, aminoethylsulfonic acid, inositol, ethylurea, citric acid or its salt, glycyrrhizinic acid or its salt, gluconic acid or its salt, creatinine, salicylic acid or its salt, tartaric acid or its salt, succinic acid or its salt, calcium acetate, sodium saccharin, aluminum hydroxide, sorbic acid or its salt, dehydroacetic acid or its salt, sodium thiomalate, nicotinic acid amide, urea, fumaric acid or its salt, macrogols, maltose, maltol, maleic acid, mannitol, meglumine, sodium desoxycholate and phosphatidylcholine, and an amorphous state-stabilizing agent selected from the group consisting of cellulose derivatives, polyvinyl pyrrolidone, cross-linked polyvinyl pyrrolidone, polyvinyl alcohol, polyvinyl acetate, vinyl alcohol/vinyl acetate copolymer, ethylene/vinyl acetate copolymer, polyethylene oxide derivatives, sodium polystyrene sulfonate, gelatin, soluble starch, pullulan, dextran, gum arabic, chondroitin sulfuric acid or its sodium salt, hyaluronic acid, pectin, chitin, chitosan, α, β, γ-cyclodextrin, alginic acid derivatives, acryl resins, polyvinyl acetal diethylaminoacetate, silicon dioxide and aluminium hydroxide, wherein the method excludes a solvent method and a mechanochemical method.

2. A method for producing a solid dispersion of a sparingly water-soluble medical substance according to claim 1, wherein the heat treating is high-frequency heating.

3. A method for producing a solid dispersion of a sparingly water-soluble medical substance comprising high-frequency heating treatment of a sparingly water-soluble medical substance and an amorphous state-stabilizing agent selected from the group consisting of cellulose derivatives, polyvinyl pyrrolidone, cross-linked polyvinyl pyrrolidone, polyvinyl alcohol, polyvinyl acetate, vinyl alcohol/vinyl acetate copolymer, ethylene/vinyl acetate copolymer, polyethylene oxide derivatives, sodium polystyrene sulfonate, gelatin, soluble starch, pullulan, dextran, gum arabic, chondroitin sulfuric acid or its sodium salt, hyaluronic acid, pectin, chitin, chitosan, α, β, γ-cyclodextrin, alginic acid derivatives, acryl resins, polyvinyl acetal diethylaminoacetate, silicon dioxide and aluminum hydroxide, wherein the method excludes a solvent method and a mechanochemical method.

4. A method for producing a solid dispersion of a sparingly water-soluble medical substance according to claim 1, wherein the amorphous state-inducing agent is aspartic acid, ethylurea, citric acid, glycyrrhizinic acid, succinic acid, aluminum hydroxide, urea, macrogols, maltol or mannitol.

5. A method for producing a solid dispersion of a sparingly water-soluble medical substance according to claim 1, wherein the amorphous state-stabilizing agent is hydroxypropylmethylcellulose (HPMC), hydroxypropylcellulose (HPC), hydroxypropylmethylcellulose-acetate succinate (HPMC-AS), methylcellulose, ethylcellulose, polyvinyl pyrrolidone, polyvinyl alcohol, ethylene/vinyl acetate copolymer, gelatin, pullulan, chitin, chitosan, sodium alginate, methacrylate copolymer or aminoalkyl/methacrylate copolymer.

6. A method for producing a solid dispersion of a sparingly water-soluble medical substance according to claim 3, wherein the amorphous state-stabilizing agent is hydroxypropylinethylcellulose (HPMC), hydroxypropylcellulose (HPC), hydroxypropylmethylcellulose-acetate succinate (HPMC-AS), methycellulose, ethylcellulose, polyvinyl pyrrolidone, polyvinyl alcohol, ethylene/vinyl acetate copolymer, gelatin, pullulan, chitin, chitosan, sodium alginate, methacrylate copolymer or aminoalkyl/methacrylate copolymer.

7. A pharmaceutical preparation containing a solid dispersion of the sparingly water-soluble medical substance obtained by the method of claim 1.

8. A pharmaceutical composition containing a solid dispersion of the sparingly water-soluble medical substance obtained by the method of claim 3.

9. A method for producing a solid dispersion of a sparingly water-soluble medical substance according to claim 1, wherein a weight ratio of the sparingly water-soluble medical substance, the amorphous state-inducing agent and the amorphous state-stabilizing agent is 1:(0.1–10):(0.1–10).

10. A method for producing a solid dispersion of a sparingly water-soluble medical substance according to claim 3, wherein a weight ratio of the sparingly water-soluble medical substance to the amorphous state-stabilizing agent is 1:(0.1–10).

11. A method for producing a solid dispersion of a sparingly water-soluble medical substance according to claim 1, wherein the process excludes the use of organic solvents.

12. A method for producing a solid dispersion of a sparingly water-soluble medical substance according to claim 3, wherein the process excludes the use of organic solvents.

* * * * *